United States Patent [19]

Krumdieck

[11] 4,170,798
[45] Oct. 16, 1979

[54] APPARATUS FOR HOMOGENIZING AND HANDLING BIOWASTE AND OTHER MATERIALS IN ISOLATION

[75] Inventor: Carlos L. Krumdieck, Birmingham, Ala.

[73] Assignee: University of Alabama in Birmingham, Birmingham, Ala.

[21] Appl. No.: 794,147

[22] Filed: May 5, 1977

[51] Int. Cl.² .......................... G01N 1/04; E03D 1/00
[52] U.S. Cl. .......................................... 4/319; 4/347; 73/421 B; 141/130; 141/329
[58] Field of Search .............. 141/130, 329, 330, 283, 141/284, 1; 73/421 R, 421 B; 4/10, 319, 320, 347; 23/253 R, 259 R

[56] References Cited

U.S. PATENT DOCUMENTS

| | | | |
|---|---|---|---|
| 820,004 | 5/1906 | MacMillan | 128/2 R |
| 3,383,923 | 5/1968 | Conche et al. | 73/421 B |
| 3,540,433 | 11/1970 | Beckman | 128/2 |
| 3,713,177 | 1/1973 | Tufts et al. | 4/10 |
| 3,718,431 | 2/1973 | Wild | 23/230 B |
| 3,727,241 | 4/1973 | Drouhard, Jr. et al. | 4/10 |
| 3,915,012 | 10/1975 | Fletcher | 73/421 R |
| 4,055,203 | 10/1977 | Crawford et al. | 141/271 |

Primary Examiner—William D. Martin, Jr.
Attorney, Agent, or Firm—Lee C. Robinson, Jr.

[57] ABSTRACT

Apparatus to receive fecal material directly into a container and maintain it isolated, particularly as to its odors, while automatically homogenizing and withdrawing samples as may be desired and disposing of the remainder. The apparatus, either in fixed or portable form, includes connections to a source of homogenization fluid, a source of cleansing water, and a drain. It also includes means to mix the fecal material vigorously with the homogenization fluid to achieve a substantially homogeneous mixture which can be disposed of with relative ease and which can be sampled into a vacutainer through a vacutainer needle attached liquid-tight to the chamber containing the mixture. For multiple sampling, an automatically operated vacutainer changer brings one vacutainer at a time into position to have a sample of the mixture injected into it. Following such sampling, the apparatus and needle are automatically washed.

5 Claims, 7 Drawing Figures

APPARATUS FOR HOMOGENIZING AND HANDLING BIOWASTE AND OTHER MATERIALS IN ISOLATION

FIELD OF THE INVENTION

This invention relates to apparatus and a method for receiving a chemical sample that is either inherently obnoxious, such as fecal matter, or for other reasons is hazardous or difficult to homogenize prior to its analysis. In particular, the invention relates to apparatus for receiving such samples in a restricted chamber, homogenizing the samples with a suitable liquid, and withdrawing measured aliquots of the homogenized material into closed individual containers containing, if necessary, suitable reagents for further analysis.

BACKGROUND OF THE INVENTION

No one who has lived through the experience will question the fact that the analysis of fecal samples is one of the most unpleasant tasks performed in a medical diagnostic laboratory. The offensive nature of the sample, combined with the inadequacy of the sampling techniques and methods available—none of which has been specifically designed to deal with fecal matter—have resulted in considerable neglect of this important area of clinical analysis.

Chapter 107 of Gradwohl's Clinical Laboratory Methods and Diagnosis, 7th ed., 1970, (one of the standard reference books) relates to the analysis of fecal samples and starts out as follows: "The examination of the feces, although generally stressed by clinical teachers as an important means of diagnosis in medical and surgical cases, is seldom thoroughly performed... most physicians are not adequately utilizing this type of examination". It then goes on to say: "The indifference to the possibilities of help from routine stool examinations, lack of concise information as to technique and interpretation, and esthetic objection to handling the material, all have contributed to this field of laboratory work being neglected by most workers and students...we believe much more emphasis must be placed on this subject".

The development of a suitable automatic apparatus for the collection, homogenization and sampling of feces would remove the esthetic objections alluded to above and permit the performance of a number of tests of obvious diagnostic and/or prognostic value. Besides, the determinations would be made quantitative (rather than qualitative or semi-quantitative as they are now) and readily automatable using autoanalyzers already in existence.

Examples of clinically important determinations that would be greatly facilitated are:

(1) Quantitative (24 hour) determination of electrolyte losses in feces. Included here are such ion as $Na^+ K^+$, $Mg^{++}$, $Ca^{++}$, P, and $Cl^-$. A better knowledge of the amount of fecal electrolyte losses can contribute greatly to the proper management of patients with acute or chronic diarrhea.

(2) Quantitative determination of fecal fat. This seldom-utilized procedure tests the ability of the gastrointestinal track to digest and absorb the fat contained in a test meal. It reflects pancreatic function as well as intestinal function. The use of radioactively labeled fats added to the test meal greatly simplifies the methodology required.

(3) Tests of intestinal absorption. One example is the determination of nitrogen content as a measure of digestion and absorption of protein. Fecal nitrogens are an essential part of nitrogen balance studies.

(4) Quantitative determination of blood losses.

(5) Determination of fecal pH.

(6) Coprocultures. There is much to be gained by the study of the "normal" flora of the intestine and its variations in response to alterations in diet composition, orally administered drugs, etc.

(7) Determination of fiber content of the feces. This is receiving increasing attention lately since it relates to the pathogenesis of syndromes as common as constipation and diverticulosis as well as carcinoma of the colon which is now the second most common cause of cancer-related deaths among American males.

(8) Quantitative determination of fecal sterols. The fecal route is the most important one for the elimination of cholesterol and its derivatives (bile acids and breakdown products thereof), and improved testing has obvious significance in the management of patients with coronary heart disease.

(9) Determination of enzyme activities in feces. Two kinds of enzymatic activities are of interest: one is the group of digestive exzymes that have been measured in feces for quite some time and are of value as tests of pancreatic and intestinal function. The other kind is non-digestive enzymes not normally present in feces but which would appear as a consequence of cell-rupture of the intestinal lining—whatever the cause. It is anticipated that these assays should provide good indicators of the presence and extent of inflammatory disease of the G.I. tract. The determination of enzymes of bacterial origin is being actively developed and promises to become a valuable tool in determining the presence of microorganisms difficult to cultivate.

(10) Presence of carcinogens and/or other hazardous compounds. Carcinogens derived from tobacco smoke are swallowed and must eventually appear in feces unless absorbed or degraded in transit. Similarly a number of other hazardous materials contaminating the intestinal environment (industrial air and water pollutants, by-products of the metabolism of intestinal microflora, etc.) should be detectable in feces presumably before permanent damage is inflected.

There are may other analyses that should be possible if suitable apparatus were available to receive and handle the samples in isolation so as to overcome reluctance by laboratory personnel to carry out existing tests and develop new tests.

OBJECT AND SUMMARY OF THE INVENTION

It is one of the objects of this invention to provide apparatus to receive and to homogenize in a limited environment fecal and other noxious material to be analyzed and means to transfer samples of the homogenized material into closed containers for further analysis.

Another object of the invention is to provide a receptacle for biowaste products and to homogenize them in the receptacle while withdrawing through a separate channel any air that enters the receptacle and is contaminated by odors therein.

A further object is to provide a biowaste receptacle capable of operating as a portable unit to be placed at the bedside of patients in order to receive waste products from such patients without requiring the patient to go to a fixed location, the receptacle being arranged to homogenize the waste and transfer samples thereof to closed containers while either sealing off the homogenization chamber or arranging circulation of the homogenate to prevent it from leaving the receptacle and, simultaneously, providing for the withdrawal of odors to prevent their contaminating the atmosphere.

In accordance with this invention a sample receptacle is provided that includes a chamber to receive material to be analyzed, particularly biowaste material, and especially fecal matter. The chamber includes an inlet for liquid, usually water, to homogenize the sample. The receptacle further includes means to inject the homogenate into a closed container, such as a vacutainer, which is an evacuated test tube provided with a resealable cap of rubber or the like through which the homogenate can be injected by a suitable hollow needle that has a side opening and a spring-biased slidable closure. After the needle has pierced the cap of the vacutainer, the homogenate enters the vacutainer by the differential pressure that results from having ambient atmospheric pressure on the homogenate and low pressure inside the vacutainer. If the homogenate is enclosed within a sealed chamber, the apparatus includes means to reduce the volume of the chamber, for example by a piston of controlled stroke in the wall of the chamber, to compensate for the quantity of material transferred to the vacutainer.

The apparatus further includes means to separate the needle and the vacutainer after a proper quantity of homogenate has been transferred. The rubber stopper of the vacutainer automatically reseals itself and the vacutainer can be removed to an analytical lab subsequent analysis. The apparatus includes means for bringing several vacutainers one after another into position to receive homogenate from the same batch.

After sufficient homogenate has been withdrawn from the homogenizing chamber, the apparatus includes means to wash the chamber and direct the remaining homogenate and the washing fluid out through a drain. The drain need not be of large size in view of the fact that the process of homogenization has reduced the original sample to particles of very small size. If the homogenizing chamber is of the type that is entirely closed during the homogenizing process, it can remain closed during the process of washing it out, and any aerosols produced can be carried down the drain. In the case of apparatus having an open homogenizing chamber dependent for containment of the sample during homogenization on the contour of the walls of the chamber and the control of circulation of the homogenate, aerosols may be extracted by vents relatively high on the wall of the bowl above the homogenizing chamber. Such vents are connected to an exhaust fan and the aerosols are forced out through a vent pipe sufficiently long and isolated to carry them away from any area where they would be objectionable.

The open-topped homogenizing chamber makes the apparatus (minus the vacutainer changer-sampler mechanism) suitable for use as a toilet in areas where water is scarce. Homogenization of fecal matter allows it to pass through a smaller drain than is usually required, and the wash water and homogenizing water required total less than the usual replacement water for a toilet bowl and tank. Also the procedure should be quieter than is usually the case in an ordinary toilet. The operating cycle for removing material from the chamber and washing the chamber can be timed differently in the case of solid waste than for entirely liquid waste, thereby effecting additional savings in the case of liquid waste, which would only require a small amount of wash water.

DESCRIPTION OF THE PREFERRED EMBODIMENTS

Figure 1:
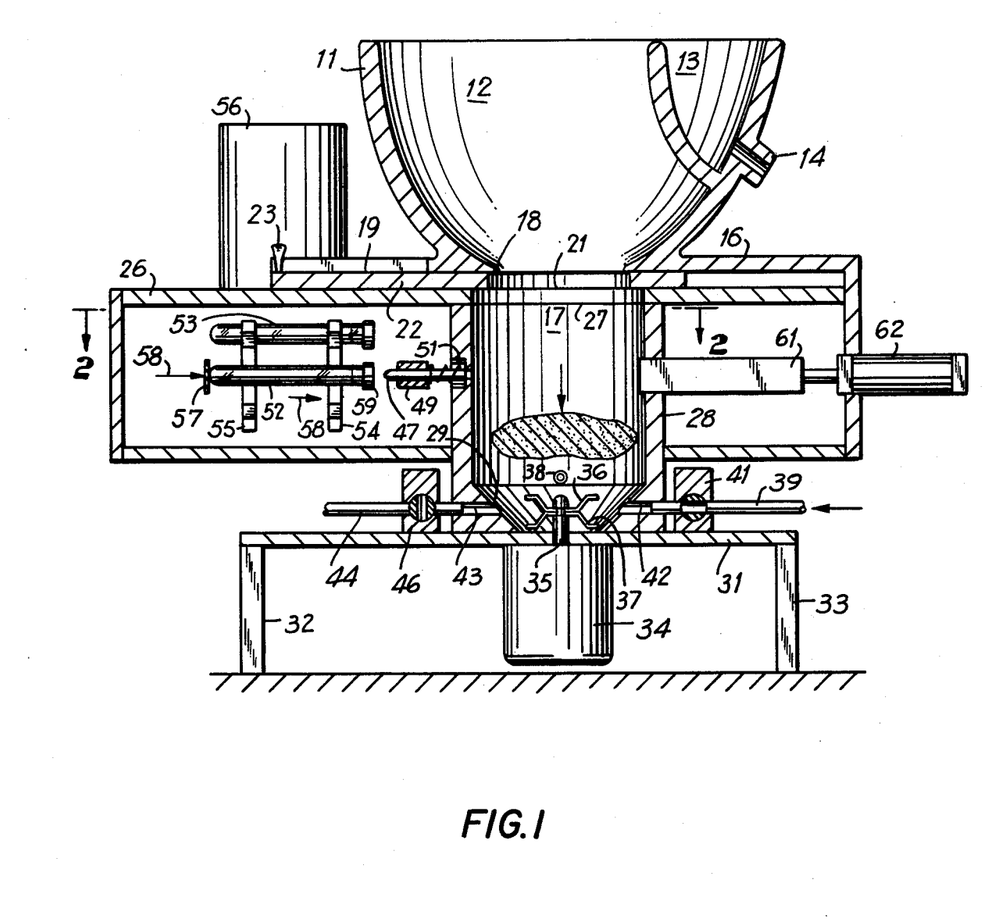
FIG. 1 is a cross-sectional view of one embodiment of a fecal sample receiver and a homogenizing chamber and basic sample withdrawal apparatus in accordance with the present invention.

The apparatus shown in FIG. 1 includes a bowl 11 divided into a main section 12 to accommodate solid fecal waste and a smaller section 13 to accommodate liquid waste. The latter section has an outlet 14 which, in use, would be connected to a drain pipe or an appropriate receptacle.

The bowl 11 is atop an enclosure 16 in which a homogenization chamber 17 is located. The homogenization chamber is directly under an opening 18 at the bottom of the section 12. At certain times of the operating cycle a sliding lid 19 having an opening 21 therein is moved either into the position shown, in which the opening 21 is concentric with the opening 18, or is moved to the left to a position in which the solid portion 22 of the lid covers the upper open part of the chamber 17 and completely isolates that chamber from the section 12 of the bowl 11. The lid 19 is slid back and forth between its two positions by a handle 23.

The bottom of the lid 19 rests on a plate 26 that has an opening 27. The bottom of the lid is in good contact with at least the edge portion of this plate that defines the perimeter of the upper opening of the chamber 17. This is desirable to prevent any of the sample from being attached to the surface of the section 22 of the lid 19 and transferred into a space between the section 22 and the plate 26.

The main wall 28 of the homogenization chamber 17 is generally cylindrical in shape and defines a frusto-conical lower portion 29 of the chamber 17. The lower end of the wall 28 rests on a support comprising a plate 31 and vertical members 32 and 33. A homogenization motor 34 is supported on the plate 31 and the shaft 35 of the motor extends through a liquid-tight opening in the plate 31. This structure includes stirring blades 36 and 37 located in the frusto-conical recess 29. The end of an inlet through which homogenization fluid enters the chamber 17 is indicated by reference numeral 38. Wash water is fed into the chamber 17 by way of a pipe 39, a valve 41, and inlet opening 42 into which the end of the pipe 39 is inserted. Unneeded sample material and water that has been used for washing the homogenization chamber 17 leave the chamber by way of an outlet 43 and an outlet pipe 44 with a valve 46 controlling the flow through the pipe 44.

The removal of aliquot samples of the homogenized material from the chamber 17 is by way of a vactuainer needle 47 that has an opening, which is not visible in FIG. 1, in its side wall. The opening is covered by a sliding cover 49 that is biased by a spring 51 compressed between a recessed part of the wall 28 and the sliding cover 49. Two vacutainers 52 and 53 are shown supported in aligned holders 54 and 55. As will be described hereinafter, a motor 56 steps the holders 54 and 55 in one direction to bring each vacutainer 52 and 53 into alignment with the needle 47. A pressure plate 57 engages one end of the vacutainer aligned with the needle 47. In the view in FIG. 1 this happens to be the vacutainer 52. When this vacutainer is pressed to the right in the direction indicated by the arrow 58, the needle 47, which may be smaller and sharper than is illustrated, pierces the rubber stopper 59 that closes the end of the vacutainer 52. A piston 61 is shown extending through the main wall 28 of the chamber 17 directly opposite the needle 47. However, such alignment is not necessary. The piston need only enter the chamber 17 at any point far enough to shift the proper volume into the vacutainer. To do so, the piston is controlled to move axially in response to operation of a motor 62.

The operation of the apparatus in FIG. 1 begins with the reception of solid fecal matter which passes through the main section 12 of the bowl 11 and the openings 18, 21 and 27 into the homogenization chamber 17. Homogenizing liquid is then allowed to enter the inlet 38 in sufficient quantity to fill the chamber 17 completely up to the level of the lower surface of the lid 19. During this step the valves 41 and 46 are both closed. Thereafter the lid 19 is closed be moving the handle 23 to the right. This movement of the lid 19 completely seals off the upper end of the chamber 17. The homogenization process is carried out by turning on the motor 34 to rotate the blades 36 and mix up the solid matter and the homogenizing liquid thoroughly. The motor is allowed to rotate for several minutes and the time may be controlled by a timer to keep the motor running long enough to effect thorough homogenization of the matter in the chamber 17.

After the homogenization is complete, the pressure plate 57 pushes to the right the vacutainer 52 shown aligned with the needle 47. As the needle pierces the rubber stopper 59 on the vacutainer, the stopper pushes on the sliding cover 49 to uncover the hole in the side of the needle. The needle itself remains fixed and only the cover slides to the right against the pressure of the spring 51. While the vacutainer may have a reduced internal pressure which would tend to draw the homogenate through the needle 47, the fact that the homogenization chamber 17 is entirely closed prevents this from happening. Instead, the piston is moved to the left a certain distance by means of the motor 62 to displace an aliquot measure of the homogenate into the vacutainer 52. Then the vacutainer is withdrawn to the left by means that will be discussed hereinafter, and the cover 49 slides back over the hole in the needle. The piston 61 does not move back to the right but remains in its displaced position until the next vacutainer, for example the vacutainer 53, is moved into position to be pushed against the needle 47. When the needle pierces the cover of the vacutainer 53 sufficiently to expose the hole in the needle to the interior of the vacutainer, the motor 62 drives the piston 61 forward another predetermined amount of transfer another aliquot measure of the homogenate into the vacutainer 53.

After a sufficient number of vacutainers have thus received homogenate, the outlet valve 46 is opened and the inlet valve 41 for the wash water is also opened to allow wash water to enter the chamber 17. The motor 34 may be energized to operate at its top speed to circulate the wash water in the chamber 17 and to allow it to flow out through the pipe 44, The motor 62 may be reversed to draw the piston back into its recessed position. Finally, to drain the chamber 17, the lid 19 may be opened to allow all of the wash water to flow out through the valve 46 and the pipe 44. At such time it is normally desirable to close the valve 41 on the inlet side of the system to prevent excess wash water from flowing into the chamber 17 and interfering with the outflow of the remaining homogenate. The process of introducing clean water into the chamber 17, circulating it to stir up any remaining homogenate and allowing the water and homogenate to flow out may be repeated as many times as necessary to clean completely the interior of the chamber 17. Thereafter, the apparatus is ready to be used by another patient.

Completely closing the chamber 17 while the homogenizing process is being carried out not only has the advantage of containing any aerosols that result from the process of the sample, but it also allows a fixed quantity of fluid to enter the chamber in order to carry out the homogenization process. As a result the assays can be referred back to a known total volume so that the results will be quantitative rather than qualitative. Moreover, the identity of content from one sample to the next of a single quantity in the chamber 13 can be maintained by keeping the motor 34 operating at a relatively slow mixing speed while the samples are being transferred to the vacutainers.

Figure 2:
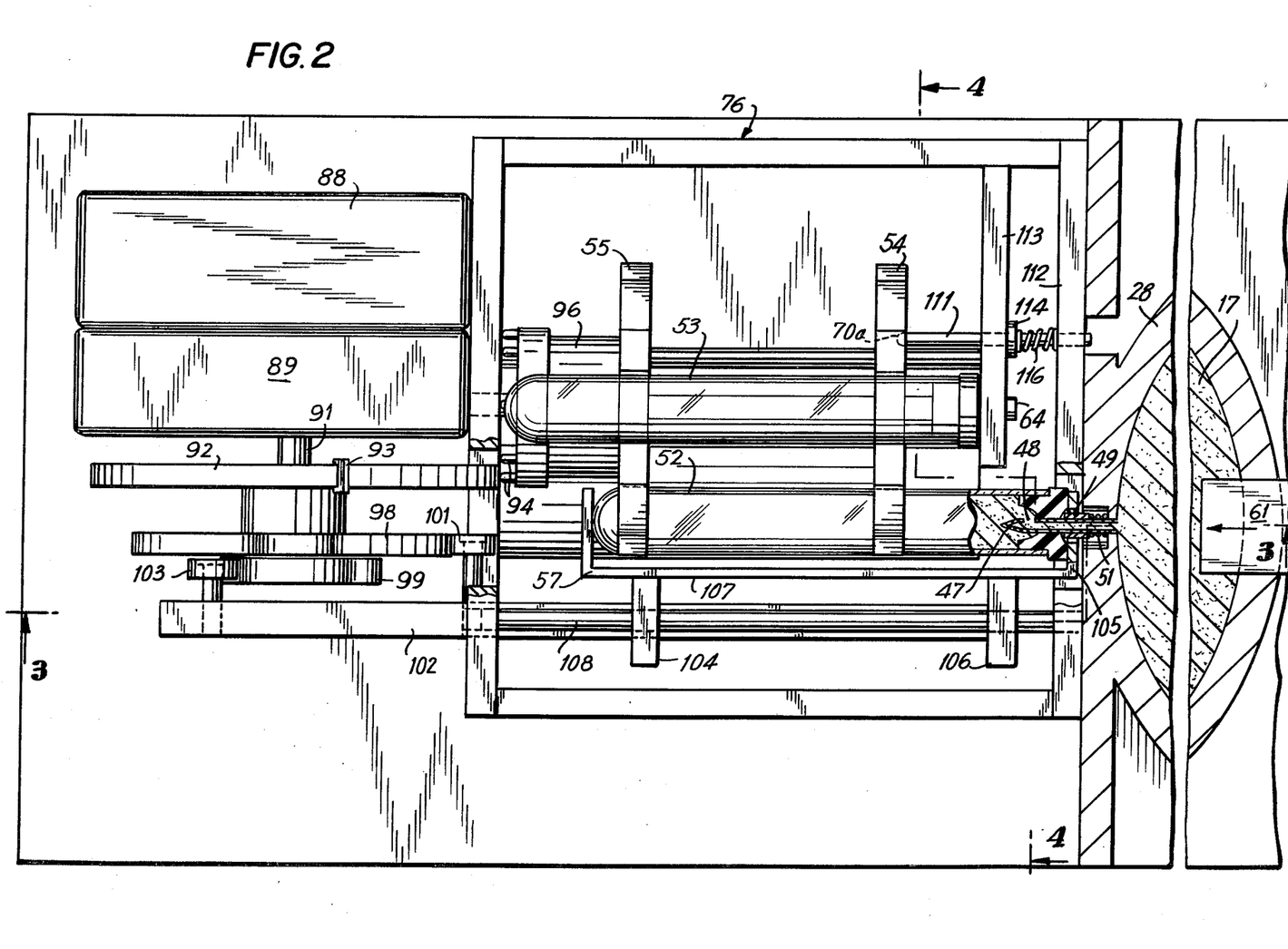
FIG. 2 is a partial cross-sectional view of the apparatus in FIG. 1 taken along the line 2—2 and illustrating particularly apparatus for bringing vacutainers into position to receive homogenate from the homogenizing chamber.
Figure 3:
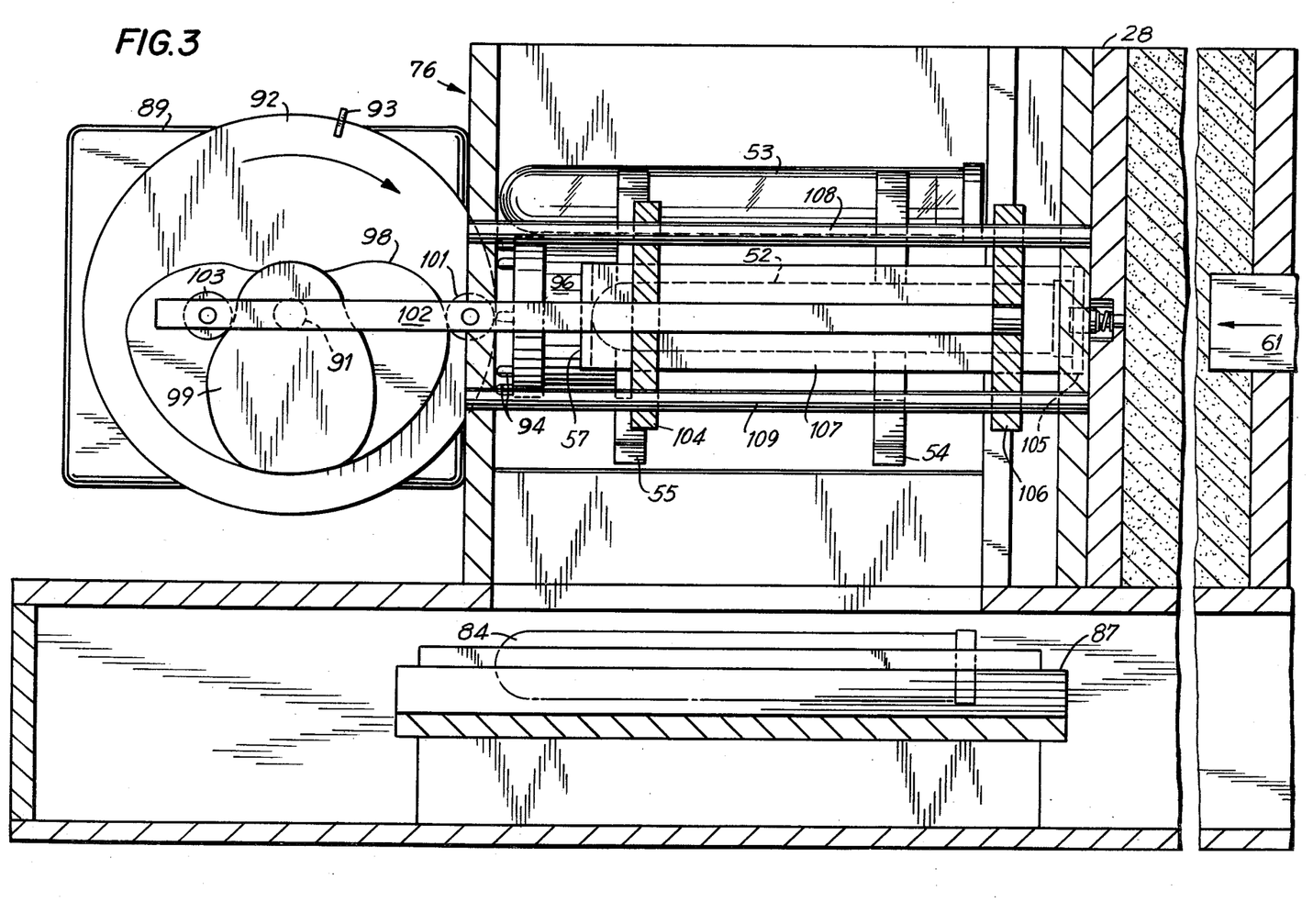
FIG. 3 is a cross-sectional view along the line 3—3 in FIG. 2 and showing the vacutainer mechanism from a different point of view.
Figure 4:
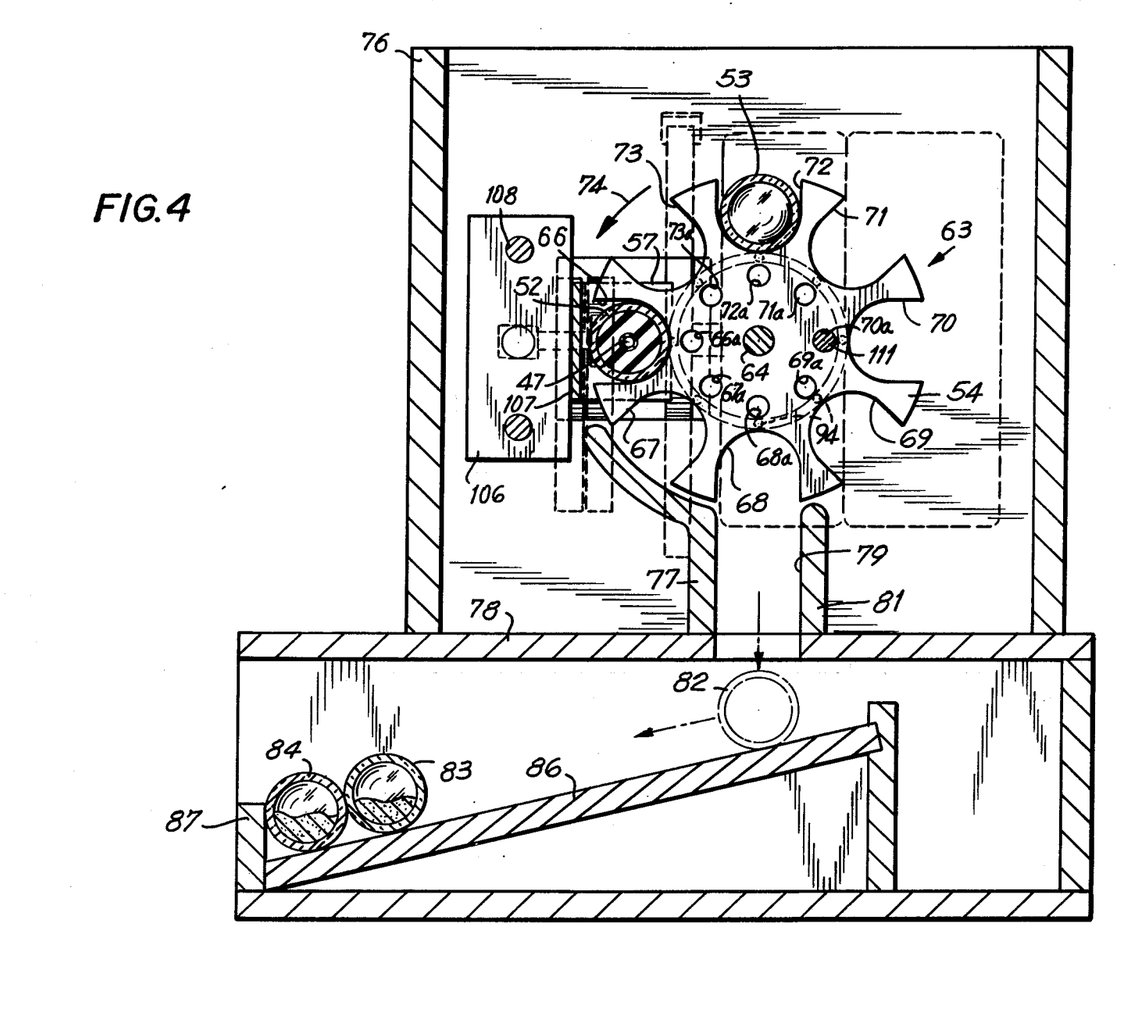
FIG. 4 is still another cross-sectional view taken along the line 4—4 in FIG. 2 and showing an end view of the vacutainer support.

The holders 54 and 55 that support the vacutainers 52 and 53 in FIG. 1 are part of a turret-like structure shown in detail in FIGS. 2-4. FIG. 4 in particular shows that turret structure 63 more clearly than the other figures. The turret comprises the two holders 54 and 55 rigidly aligned to rotate as a unit on a central rod 64. The holders 54 and 55 are notched discs, each of which has, in this embodiment, eight recesses 66-73, each of the proper size to hold a vacutainer, although only the two vacutainers 52 and 53 are shown, and these are in the recesses 66 and 72. The direction of rotation of the turret 63 is counterclockwise, as indicated by the arrows 74, and is accomplished by apparatus that will be described in connection with other figures.

The turret 63 shown in FIG. 4 is located in an open-topped box 76. Empty vacutainers will be fed by gravity from a magazine-like container. At the time depicted in FIG. 4 the uppermost recess happens to be the recess 72 in which the vacutainer 53 has been placed. As this uppermost recess rotates to the position of the recess 73, any vacutainer resting in it would remain in place simply by the force of gravity. However, at the third position, the recess 66 occupied by vacutainer 52, additional means are placed alongside the recess to hold the vacutainer in place. The additional means are associated with pushing the vacutainer into position so that its self-sealing rubber stopper 59 can be pierced by the needle 47, and this part of the apparatus will also be described in connection with other figures.

As the turret 63 moves still another step, to the position of the recess 67, any vacutainer in that position would fall out, except for the fact that a flange 77 extending upwardly from a base 78 curves around the turret 63 to support any vacutainer in the position of the recess 67.

At the next step of the turret, any vacutainer in the position defined by the recess 68 would be directly over an exit slot 79 defined between the curved flange 77 and a second, vertical flange 81. Vacutainers 82-84 that have fallen through the slot 79 land on a sloping support 86 of suitably soft material and roll safely to rest at the lower end against a low wall 87. The vacutainer 82 is depicted in broken lines to indicate that it is in motion from the turret 63 to the support 86. Vacutainers 83 and 84 are shown partially filled with homogenate from the chamber 17 and may also contain a suitable reagent to test the solid matter for any of the ions or chemicals that might be contained therein. In any event, the material to be tested will have reached the vacutainers without having to be handled by laboratory personnel. Furthermore, the vacutainers 83 and 84 can be transferred to other apparatus while still keeping the homogenized material enclosed.

The mechanism for pushing each vacutainer axially into engagement with the needle 47 is best shown in FIGS. 2 and 3. In particular, in FIG. 2 a regular motor 88 operating through a speed-reducing gear box 89 rotates a shaft 91 on which are mounted a turreet actuator disc 92 with an actuator member 93 projecting therefrom. Because of the speed reducing provided by the gear box 89, a relatively high speed motor 88 may be used instead of the low speed motor 56 in FIG. 1. This actuator member 93 engages each of a series of pins 94 extending from the turret mechanism, which, as shown in greater detail here than in FIG. 4, includes a short, thick cylinder 96, the two members 54 and 55, and the central shaft 64 on which the two members 54 and 55 are rigidly mounted.

The shaft 91 also engages a cam mechanism comprising a first cam 98 and a second cam 99. The layout of these cams is best shown in FIG. 3. The cam 98 engages a roller-follower 101 attached to a bar 102, and the cam 99 engages a roller-follower 103 that is also attached to the bar 102. The configurations of cams 98 and 99 are such that the follower 101 pushes the bar 102 to the right and the follower 103 pulls the bar 102 to the left. These are the two motions required to push a vacutainer, for example, the vacutainer 52, into engagement with the needle 47 and to retract it from such engagement.

The bar 102 has two members 104 and 106 rigidly connected to it and connected, in turn, to a member 107 that has two bent ends to grasp the vacutainer 52 between them. One of these bent ends was identified in connection with FIG. 1 as the pressure plate 57. The length of the member 107 is such that its other bent end 105 is adjacent the stopper 59 of the vacutainer. The end 105 thus enables the member 107 to retract the vacutainer 52 away from the needle 47 after the vacutainer has received liquid or homogenate through the needle.

The bent end 105 may extend over only a part of the stopper 59 so as not to prevent the needle 47 from piercing the stopper 59 when movement of the member 107 and its bent pusher end 57 force the stopper against the needle. Alternatively, and as shown in the present embodiment, the bent end 105 may have a central opening through which the needle 47 pierces the resealable stopper 59. The central opening in the bent end 105 is also large enough to allow the sliding, resiliently biased cover that normally extends over the opening 48 in the side of the needle 47 to be forced to retract only when it engages the stopper 59. This prevents the opening 48 from being uncovered before it has entered the stopper 59, which is important to prevent leakage of the homogenate outside the stopper. Furthermore, the resiliently biased cover can either be a sleeve 49 biased by a spring 51, as shown, or a close-fitting tubing of rubber or the like around the needle 47. Each vacutainer is brought into position between the members 57 and 105 by rotation of the turret 63 when the bar 102 is in its retracted position farthest to the left. The members 104 and 106 slide linearly on two rigidly mounted guide rods 108 and 109 that prevent the members 104 and 106 from turning on the bar 102. In addition, the bar may be square or rectangular to assist in holding the members 104 and 106 correctly positioned.

The turret mechanism also includes a detent mechanism, which is most clearly shown in FIG. 2. This includes a detent pin 111 slidably mounted in two plates 112 and 113 at the end of box 76 housing the vacutainer actuating structure. The plate 113 is rigidly mounted in the box 76 parallel to the plate 112 to support one end of the turret shaft 64. The detent pin has a collar 114 rigidly mounted on it and a spring 116 that presses against the collar 114 and against the plate 112 to urge the collar against the plate 113 and thereby to urge the pin 111 into limited engagement with the member 54. By means of the detent mechanism, and suitably located detent depressions, each at a fixed position relative to each of the recesses 66-73, the rotation of the turret 63 and the members 54 and 55 can easily be locked at each step so that each vacutainer in turn will be brought specifically into alignment with the needle 47. These depressions are identified in FIG. 4 by the reference numbers 66a-73a corresponding to the recesses 66-73 with which they are aligned.

FIGS. 2 and 3 show a convenient location for the piston 61. As previously stated, this piston need not be directly opposite the needle 47 since the only purpose of the piston is to decrease the volume of the chamber 17 by a specific amount corresponding to the amount of sample transferred to each vacutainer in turn. This reduction in the volume of the chamber 17 could be accomplished by mounting the piston 61 at any point in the chamber wall.

Figure 5:
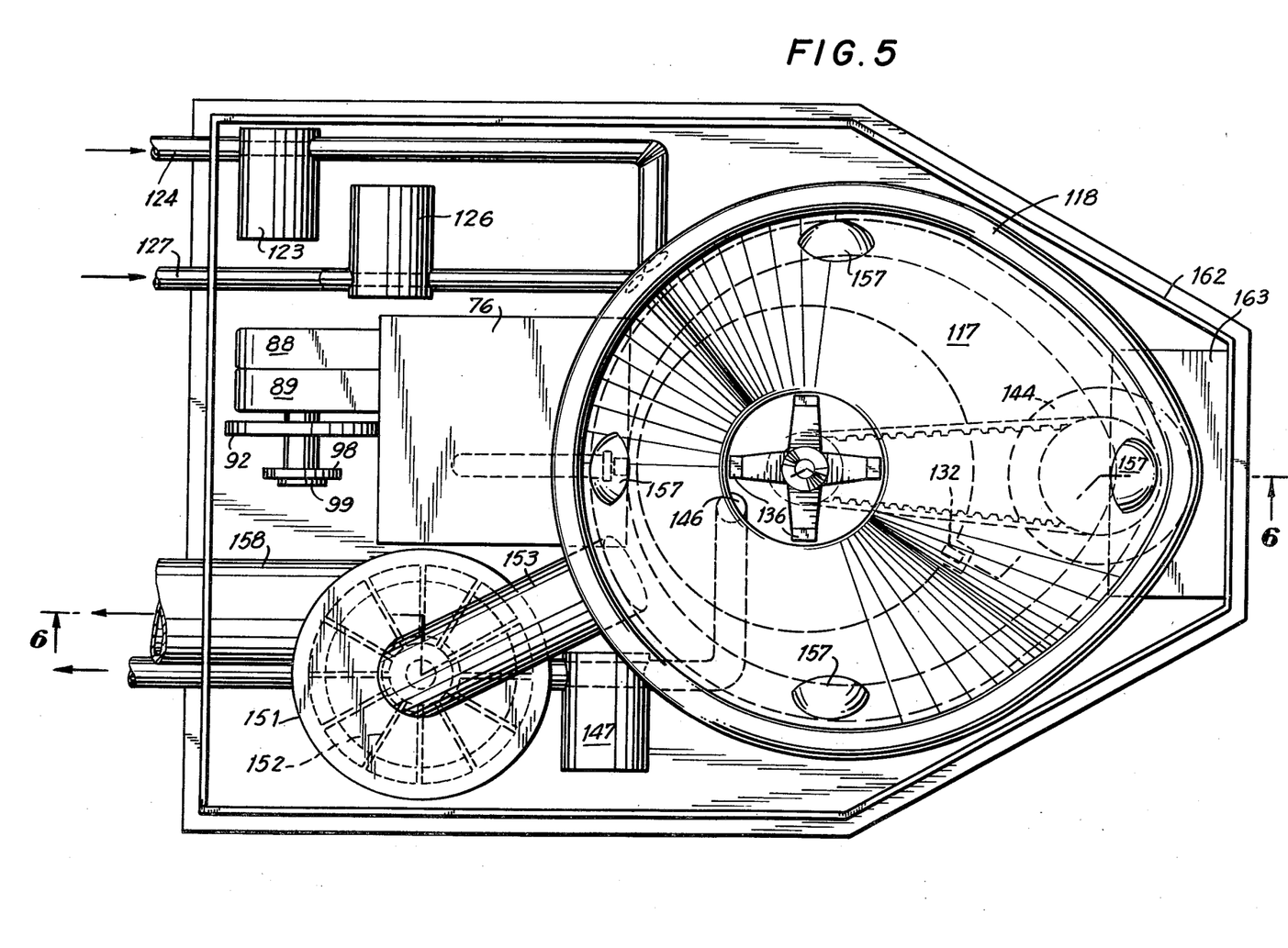
FIG. 5 is a plan view of apparatus to operate as a toilet or fecal sample receiver in accordance with this invention.
Figure 6:
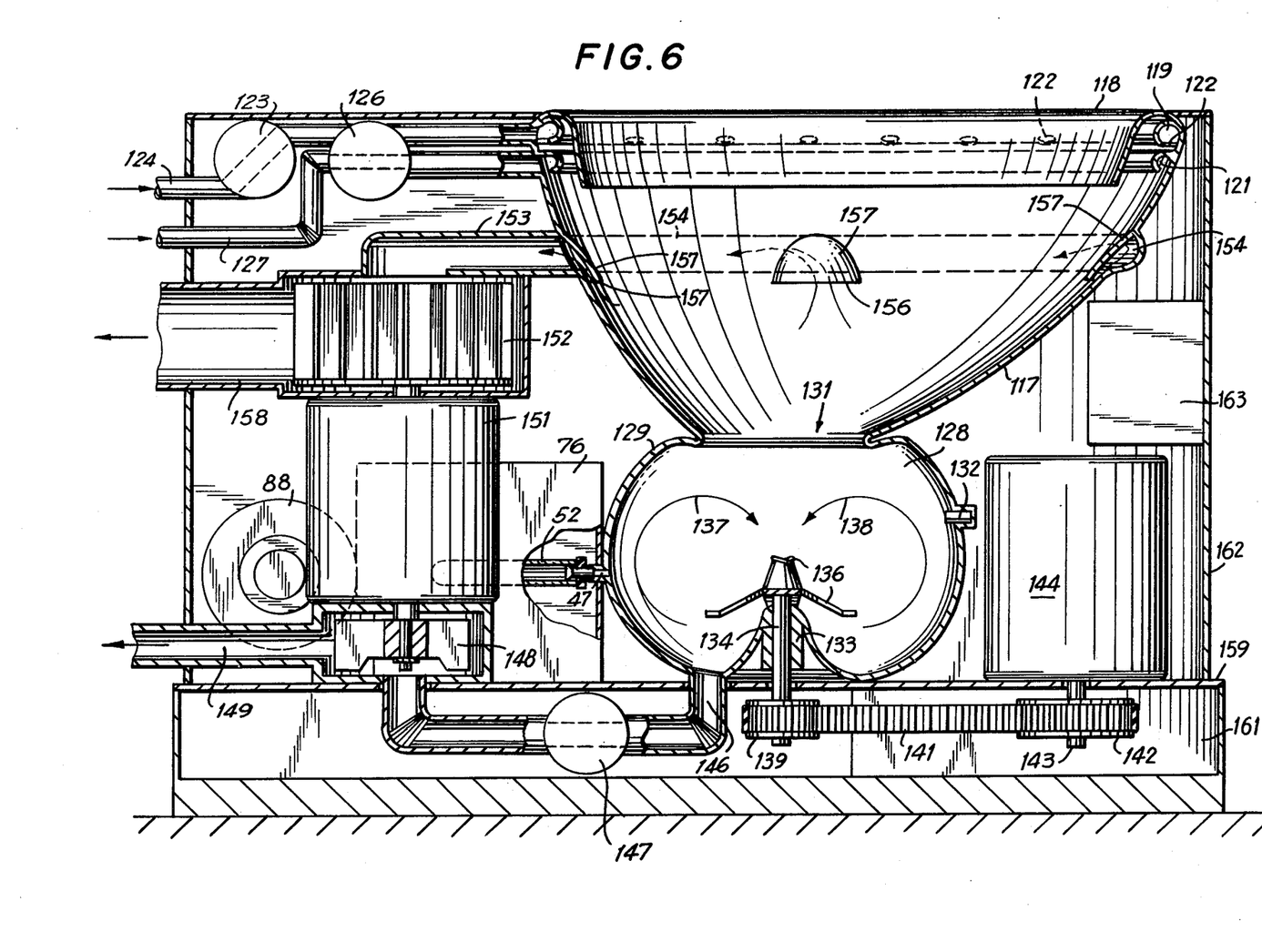
FIG. 6 is a cross-sectional side view of the apparatus in FIG. 5 along the lines 6—6 in FIG. 5.

FIGS. 5 and 6 show an alternative embodiment of the invention to carry out the same functions as the embodiment in FIGS. 1-4. The uppermost part of the structure in FIGS. 5 and 6 is a bowl 117 having a shape similar to a standard toilet bowl. The upper edge of the bowl 117 is formed as an in-turned and down-turned rim 118 that extends over a pair of channels 119 and 121. The channel 119 is generally closed except for spaced holes 122 and is connected by way of a solenoid inlet valve 123 to a water supply pipe 124. The channel 121 has a U-shaped cross section along its length and is connected by way of a homogenization fluid solenoid valve 126 to a pipe 127 to a source of the homogenization fluid, which may be water.

The lower part of the bowl 117 terminates in a homogenization chamber 128 defined by a wall 129 and connected by way of a restricted opening 131 to the lowermost part of the bowl 117. A fluid level sensor 132 is located in the wall 129 at a predetermined level above the level of the needle 47 to measure the proper level of the homogenization fluid. A water-tight gland 133 centrally located in the lower part of the chamber 128 allows a shaft 134 to rotate therein without permitting any liquid to leak back along the shaft. A set of homogenization blades 136 is attached to the end of the shaft 134 to be rotated thereby. The ends of the blades 136 are twisted in a manner similar to a propeller to force fluid in the homogenization chamber 128 to follow a generally toroidal path virtually entirely within the chamber 128 as indicated by arrows 137 and 138. The other end of the shaft 134 is connected by a positive drive pulley 139 and a correspondingly shaped driving belt 141 to drive pulley 142 mounted on a shaft 143 of a homogenizer motor 144.

An outlet pipe 146 is connected to one part of the lowermost section of the wall 129 and a discharge solenoid valve 147 in this pipe controls the discharge of material from the chamber 128. The flow of discharged material is effected by a pump 148 to provide positive transfer of outlet fluid from the pipe 146 to a drain 149.

The pump 148 is driven by a motor 151 that also drives a centrifugal fan 152. This fan is connected by a pipe 153 to a manifold 154 that has several intake openings 156 spaced around the bowl 117 above the constricted opening 131 at the top of the homogenization chamber 128. The upper part of each of the openings 156 is covered by a flap 157 to allow air to enter the openings 156 primarily from below. Air can be drawn into the openings 156 and on out the vent pipe 158 by the fan 152 after the air enters the upper part of the bowl 117. The flow will be such that this air will circulate down to the lower part of the bowl and will pick up any aerosols emanating from the chamber 128. This effectively seals objectionable odors in the chamber 128 to make this embodiment as acceptable as the embodiment in FIG. 1. The flaps 157 also prevent any liquid entering the bowl 117 by way of the water supply pipe 124 or the homogenization fluid pipe 127 or any other source from flowing into the ventilating system.

The motor 88, including the gear mechanism 89 and the vacutainer changing disc 92 along with the cams 98 and 99 shown mounted on the enclosure 76 in FIG. 5 are the same as shown in FIGS. 1-4. These drive components for filling the vacutainer 52 through the needle 47 in FIG. 6 operate exactly as described in connection with the embodiment in FIGS. 1-4 except that since the homogenization chamber 128 has no lid similar to the lid 19 of the chamber 17 in FIG. 1, it is not necessary to provide a piston similar to the piston 61 in FIG. 1 to control the quantity of homogenate transferred to one of the vacutainers 52.

The bowl 117, the motors 144 and 151, the vacutainer changer and filler mechanism in the enclosure 76 and all of the other components connected therewith are supported on a platform 159 that has an enclosed chamber 161 within which the pulleys 139 and 142, the belt 141, the outlet pipe 146 and the solenoid valve 147 are located. On top of the platform 159 is another enclosure 162 that encloses all of the other mechanism associated with the bowl 117 and the various motors and valves and pipes. A programmed timer 163 is also located within the enclosure 162 and is connected to control the sequential operations of the various motors and valves.

Figure 7:
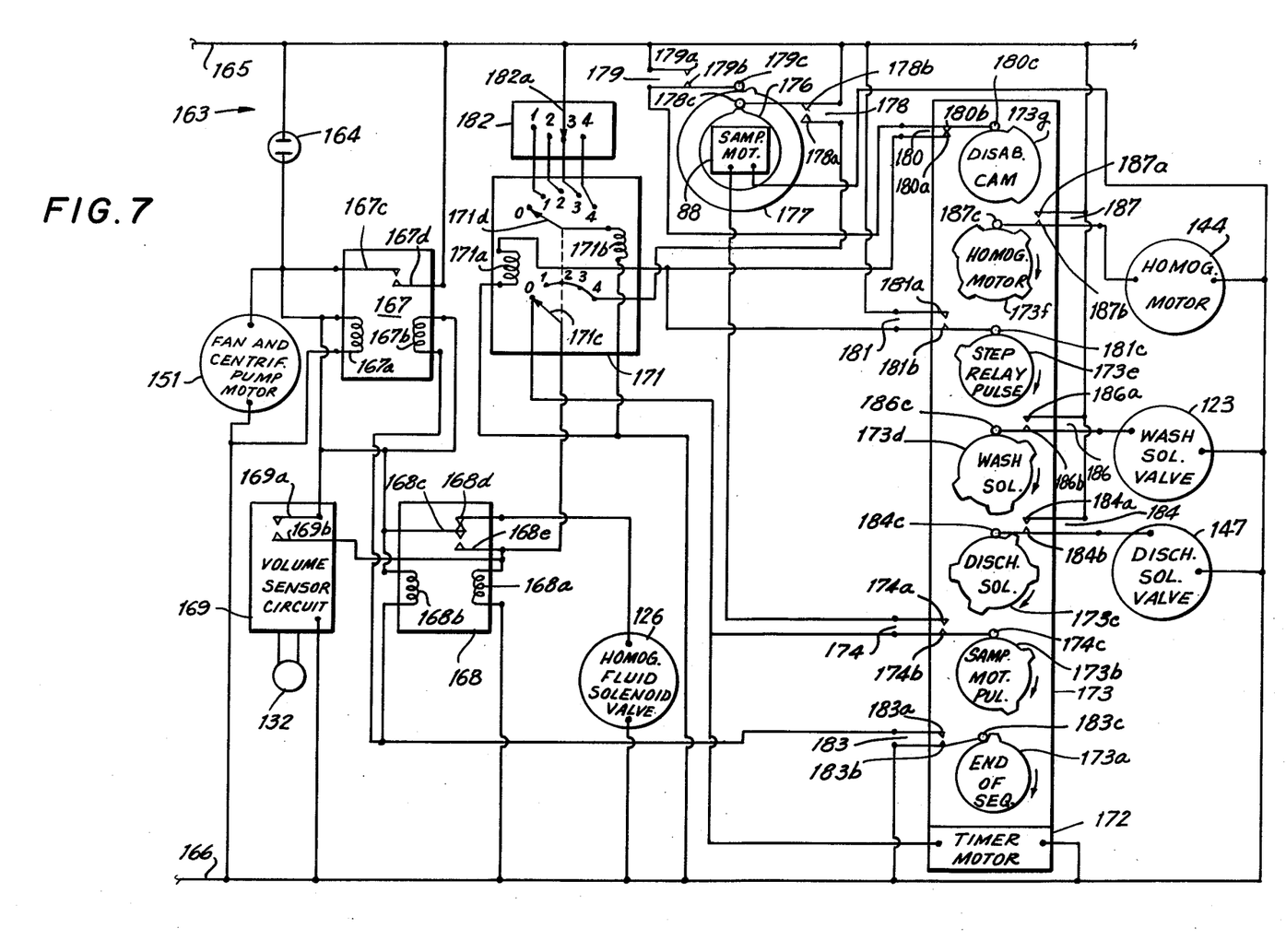
FIG. 7 is a circuit diagram for operation of the apparatus in FIGS. 5 and 6.

FIG. 7 shows the electrical circuit for the programmed timer 163. This circuit includes a pushbutton starting switch 164 connected in series with the fan and centrifugal pump motor 151 between two wires 165 and 166 of a standard 110 v AC line. The latching coil 167a of a latching relay 167 is electrically connected directly in parallel with the motor 151 and in series with the pushbutton switch 164. The latching relay includes an unlatching coil 167b and a movable contact 167c that is caused to engage a fixed contact 167d when the relay is in its latched condition. The contacts 167c and 167d are connected directly in parallel with the pushbutton switch 164.

The pushbutton switch 164 is also connected to a movable contact 168c of a second latching relay 168. This relay has a latching coil 168a and an unlatching coil 168b. It also has two fixed contacts 168d and 168e to be contacted by the movable contact 168c, depending on whether the relay is unlatched or latched. The contact 168d is connected in series with the homogenization fluid solenoid valve 126.

The volume sensor 132 is connected through a standard sensor electronic circuit 169 to control the opening and closing of a pair of contacts 169a and 169b. These contacts are closed when the volume of the water in the chamber 128 shown in FIG. 6 is sufficient to actuate the sensor 132. Closing of the contacts 169a and 169b connects the latching coil 168a in a series circuit with the contacts 167c and 167d between the two wires 165 and 166 of the 110 v line, thereby attracting the contact 168c into engagement with the fixed contact 168e.

The contact 168e is connected to the arm 171c of a 5-position, 2-layer stepping relay 171. The relay 171 has a stepping coil 171a and a resetting coil 171b. The arm 171c is mechanically connected to another arm 171d. The first position marked "0" of the terminals engaged by the arm 171c is connected to one terminal of a timer motor 172, the other terminal of which is connected to the AC wire 166. This timer motor is mechanically connected to a multi-cam timer 173, each cam of which engages at least one movable arm to control the opening and closing of at least one switch connected to that arm. The timer 173 in this embodiment has seven cams 173a–173g.

The sampler motor 88 that controls rotation of the turret 63 which was described particularly in connection with FIG. 2 in which the vacutainers are held and also controls the axial movement of the vacutainers into engagement with the needle 47 and away from it, is electrically connected between one of the AC wires 166 and a fixed contact 174a of a switch 174. This switch has a movable contact 174b controlled by a roller-follower 174c that engages the surface of the cam 173b to bring the contacts 174a and 174b together each time the follower is lifted by one of the raised portions of the cam 173b.

The sampler motor 88 also drives two cams 176 and 177. A switch 178 has a fixed contact 178a and a movable contact 178b connected to a cam-follower 178c to be controlled by the cam 176. One of the contacts of the switch 178 is connected to the AC wire 165, and the other contact of the switch 178 is connected to one terminal of the motor 88 and is also connected to all but the first of the five position contacts of the set engaged by the arm 171c. Another switch 179 is controlled by the cam 177 driven by the sampler motor 88. The switch 179 has a fixed contact 179a and a movable contact 179b attached to a cam-follower 179c that engages the cam 177. One end of the stepping coil 171a of the stepping relay 171 is connected directly to one of the AC wires 166 and the other end of the coil 171a is connected through a switch 180 to one of the contacts of the switch 179, the other contact of which is connected to the other AC wire 165. The latter end of the coil 171a is also connected through a switch 181 to the AC wire 165. The switch 181 includes a fixed contact 181a and a movable contact 181b controlled by a cam-follower 181c that rides on the surface of the cam 173e. The switch 180 includes a fixed contact 180a and a movable contact 180b controlled by a cam-follower 180c that rides on the surface of the cam 173g.

One end of the resetting coil 171b of the stepping relay 171 is connected to the AC wire 166 and the other end of the coil 171b is connected to the arm 171d of the five-position stepping switch on the second layer of the relay 171. The first position, marked "0", engaged by the arm 171d is not connected to any other circuit part, but the second through fifth terminals engaged by the arm 171d and labeled, respectively, "1, 2, 3, 4" are connected to correspondingly marked terminals "1, 2, 3, 4" of a manually controlled switch 182. This switch has an arm 182a connected to one AC wire 165.

A switch 183 is connected in series between one terminal of the unlatching coil 167b of the latching relay 167 and the AC wire 166. This switch includes a fixed contact 183a and a movable contact 183b attached to a cam-follower 183c to be controlled by the cam 173a. The switch terminal 183a connected to one end of the coil 167b is also connected to one end of the unlatching coil 168b of the relay 168.

The discharge solenoid valve 147 shown in FIGS. 5 and 6 is shown in FIG. 7 to be electrically connected in series with a switch 184 between the two AC wires 165 and 166. The switch 184 includes a fixed contact 184a and a movable contact 184b attached to a cam-follower 184c controlled by the cam 173c. In a similar manner the wash solenoid valve 123 is connected in series with a switch 186 between the two AC wires 165 and 166. This switch includes a fixed contact 186a and a movable contact 186b mechanically connected to a cam-follower 186c to be controlled by the cam 173d. The homogenization motor 144 is also connected in series with a switch 187 between the two AC wires 165 and 166. This switch 187 includes a fixed contact 187a and a movable contact 187b mechanically attached to a cam-follower 187c to be controlled by the cam 173f.

The operation of the apparatus in FIGS. 5 and 6 as controlled by the circuit in FIG. 7 starts with actuation of the pushbutton switch 164 to complete the circuit to energize the fan and centrifugal pump motor 151 and to latch the relay 167. This closes the contacts 167c and 167d to keep the fan and pump motor 151 operating even after pressure on the pushbutton switch 164 is released.

The homogenization fluid solenoid valve 126 is also actuated at the same time that the relay 167 is latched. The actuation of the homogenization fluid solenoid valve is by way of the movable contact 168c of the unlatched relay 168 and the fixed contact 168d connected to the valve 126. This allows fluid to enter the homogenization chamber 128 by way of the valve 126 until the fluid rises to a level that actuates the sensor 132. This controls the electronic circuit 169 to close the contacts 169a and 169b, thereby latching the relay 168 and moving the arm 168c away from the contact 168d to cut off energizing current to the homogenization fluid solenoid valve 126.

When the contact 168c responds to the latching of the relay 168, it moves into contact with the fixed terminal 168e and thus, by way of the arm 171c of the stepping relay 171 and the "0" terminal of that relay, it starts the timer motor 172. As the timer motor 172 rotates the cams 173a–173g clockwise, the homogenization motor cam 173f forces the cam-follower 187c to close the contact 187b against the contact 187a and thereby energize the homogenizer motor 144. The homogenizer motor cam 173f keeps the switch 187 closed for a relatively long time and at the end of this time the cams have rotated sufficiently to cause the stepping relay pulse cam 173e to close the switch 181 and thereby energize the stepping coil 171a to move the arms 171c and 171d one step in the clockwise direction to their respective terminals marked "1". This brings the arm 171c into position to start the sampler motor 88 through a circuit that includes the arm 171c, the fixed terminal 168e of the relay 168, the movable arm 168c, and the contacts 167c and 167d of the latching relay 167.

Energization of the sampler motor 88 causes the cams 176 and 177 to start rotating in a clockwise direction, thereby releasing the cam-follower 178c to close the contacts of the switch 178 and to keep the sampler motor running. The stepping relay pulse cam causes the contacts of the switch 181 to remain closed for only a short time so that the stepping pulse is relatively short. This actuation of the stepping coil 171a moves both of the arms 171c and 171d from their respective "0" positions to their respective "1" positions. As a result, current to the timer motor 172 is interrupted and the cams 173a–173g are stopped. The cam 173f stops in a position that keeps the homogenizer motor 144 operating during the following sampling process and until the motor 172 starts to rotate again.

The sampling process controlled by the sampler motor 88 moves the vacutainers into engagement with the needle 47 one at a time, retracts them, and rotates the turret 63 another step to repeat the process. As the sample motor 88 rotates, the cam 176 briefly opens the switch 178, but the sampler motor is still energized through the switch arm 171c. The cam 177 briefly closes the switch 179 just before the brief opening and reclosing of the switch 178 and thereby delivers a short stepping pulse to the stepping coil 171a to move the arms 171c and 171d to their "2" contact. The switch arm 182a is set to allow samples to be obtained in three vacutainers and so is placed on its "3" contact. As a result, when the sampler motor makes its third rotation in connection with transferring a sample to the third vacutainer, the resetting coil 171b of the stepping relay 171 causes the arms 171c and 171d to return to their "0" positions. This allows the timer motor 172 to be energized again by way of the arm 171c.

As the timer motor 172 again starts to rotate, it rotates the cams 173a–173g and turns off the homogenizer motor 144 by allowing the contacts of the switch 187 to open. Shortly after that the cam 173c causes the discharge valve 147 to open and allow the remainder of the homogenate to be drawn out by the pump 148 and sent through the drain pipe 149. The fan and centrifugal pump motor 151 remains operating during the entire cycle.

After the discharge valve 147 has been opened for the first time, the cam 173c allows the switch 184 to reopen and to de-energize the valve 147. Then the cam 173d closes the contacts of the switch 186 and energizes the wash solenoid valve 123 to allow clean water to flow down the bowl and into the homogenization chamber 128. While this water is in the chamber, the cam 173f again closes the switch 187 to energize the homogenization motor 144 a second time. Thereafter the homogenizer motor is turned off by the effect of the cam 173f in reopening the switch 187, and the discharge solenoid valve is again energized as the cam 173c closes the switch 184 for a second time. During the time that this valve is open, the cleansing wash water is drawn through the centrifugal pump 148 and expelled through the drain.

The continued rotation of the cams 173 causes the cam 173d to close the switch 186 a second time and open the wash solenoid valve 123 to allow a new quantity of rinsing water to wash down the bowl and enter the chamber 128. The cam 173f closes the switch 187 during the time and energizes the homogenizer motor 144 to stir up the wash water. The sampler motor cam 173b then closes the switch 174 for a brief interval pulsing the sampler motor 88 into operation. The sampler motor runs for a complete cycle of sampling of one vacutainer. This provides the first wash of the inside of the sampling needle 47 as shown in FIG. 6. The wash water in this case goes into an extra vacutainer inserted into the members 54 and 55 solely for the purpose of receiving the water that washes the needle.

At the same time that the switch 174 is closed, the cam 173g opens the switch 180 and holds it open until the end of the operating sequence. This prevents current pulses from flowing through the switch 179 to the stepping coil 171a and causing the arms 171c and 171d to step forward until a new sequence has started.

At the end of the cycle of operation of the sampler motor 88 when the first washing of the needle takes place, as has just been described, the opening of the switch 178 stops the motor 88. By that time the timer motor 172 will have driven the cams 173 past the point at which the cam 173b can close the switch 174. Continued rotation of the motor 172 causes the cam 173c to close the switch 184 again to open the discharge valve 147 and allow water in the chamber 128 to flow out the drain 149. The discharge valve 147 closes again when the cam 173c rotates farther and allows the switch 184 to open.

A second needle-washing cycle is then carried out in a manner similar to the first such cycle. That is, continued rotation of the cams 173 by the timer motor 172 causes the cam 173d to close the switch 186 and energize the wash solenoid valve 123. This permits a new quantity of water to flow into the chamber 128. The cam 173f then closes the switch 187 to start the homogenizer motor 144 again. The cam 173b then closes the switch 174 briefly again to supply another pulse to operate the sampler motor 88 for another cycle. The water for the second cleansing of the needle will go into still another vacutainer placed in a recess in the holders 54 and 55 for that purpose.

At the completion of rotation of the sampler motor 88 following the second needle washing cycle, the cam 173c again closes the switch 184 to open the discharge valve 147 and allow the remaining water to flow out the drain 149. The final event of a complete testing sequence occurs when the cam 173a closes the switch 183 and thereby completes the circuits through the unlatching coils 167b and 168b to release both of the latched relays 167 and 168 to turn off the entire circuit.

A typical time for homogenizing a fecal sample, transferring the homogenate to five vacutainers, and completing the automatic cleansing of the apparatus is approximately three or four minutes. During the entire procedure, the sample will be isolated from the hospital personnel, from the time of sample collection through the final steps of analysis.

The apparatus as embodied in either FIG. 1 or FIGS. 5 and 6 can be operated as a portable toilet with suitable connections to vents, drains, water lines, and power lines, or it can be placed in a fixed location, in which case the connections can be of a more permanent nature.

While the open-topped chamber 128 in the embodiment in FIGS. 5 and 6 does not provide quite as rigid control of the volume as the container 17 with its lid 22 in FIG. 1, the difference in accuracy of measurement of the total homogenization volume is not significant. The results are still well within the range of accuracy necessary to constitute quantitative analysis of the sample. The most significant difference in this regard between the embodiment in FIG. 1 and that in FIGS. 5 and 6 is that the piston 61 can be used only in the embodiment in which the container is sealed liquid-tight by the lid 22. Use of the piston allows more accurate control of the quantity of homogenate allowed to enter the vacutainers.

Under certain circumstances it may be required to control the speed of the homogenizer motor 34 in FIG. 1 or the homogeizer motor 144 in FIGS. 5 and 6. This can be done by means of a standard silicon-controlled rectifier circuit arranged to cause the motor speed control circuit to vary, for example, from a high initial homogenization speed to a lower stirring speed to keep the mixture stirred up during the sampling process.

While this invention has been described in terms of specific apparatus, it will be understood that modification may be made therein and that the true scope of the invention is determined by the following claims.

What is claimed is:

1. Apparatus for receiving and processing noxious material, the apparatus comprising:
   a container comprising an upper opening through which a quantity of the noxious material passes into the container;
   means to mix the material in the container with a controlled quantity of liquid to form a relatively homogeneous mixture of the liquid and particles of the material;
   an enlarged section extending upwardly from the container and joined liquid-tight to the container around the upper opening;
   means to limit aerosols within the container from rising out of the apparatus, the aerosol limiting means including a manifold supported on the enlarged section and an exhaust fan connected to the manifold to draw the aerosols out of the apparatus by way of the manifold;
   a sample receiver comprising a self-resealing resilient water-tight closure member; and
   means attached liquid-tight to the container to inject a quantity of the mixture into the sample receiver through the self-sealing closure member.

2. Apparatus for receiving and processing noxious material, the apparatus comprising:
   a container to receive a quantity of material to be mixed and comminuted in the container with a controlled quantity of homogenizing liquid;
   homogenizing means within the container to comminute and agitate vigorously the material and the homogenizing liquid to form a homogeneous mixture of the liquid and particles of the material;

a plurality of vacutainers for receiving samples of the mixture, each of the vacutainers having a self-resealing stopper;

injection means connected liquid-tight to the container;

means to control the injection means to inject controlled quantities of the mixture into said vacutainers through their stoppers, the means to control the injection means comprising a rotary turret having a plurality of vacutainer-holding means, one for each of said vacutainers, means to rotate the turret in steps to align one of the vacutainers at a time with the injection means, and means to move the aligned vacutainer axially in one direction to force the injection means through the stopper of that vacutainer to allow the mixture to flow through the injection means into the vacutainer, and then to move the aligned vacutainer in the opposite direction to withdraw that vacutainer from the injection means, the injection means comprising resiliently biased sealing means to prevent leakage of the mixture when the injection means is not inserted through a vacutainer stopper.

3. The apparatus of claim 2 in which the means to control the injection means further comprises:
a liquid-tight closure for the container; and
a piston controlled to displace a predetermined volume of the mixture injected into a vacutainer.

4. Apparatus for treating relatively solid biowaste material, the apparatus comprising:
a biowaste receiver comprising an upper section shaped like a toilet bowl and an integrally connected lower section of generally toroidal configuration and a constricted opening between the upper and lower sections;
rotary stirring means in the lower section to produce a generally toroidal agitation of liquid and biowaste material to produce a substantially homogeneous mixture thereof;
a sample receiver externally disposed with respect to the lower section and movable into close juxtaposition therewith;
means for discharging a controlled quantity of the homogeneous mixture from the lower section into the sample receiver;
duct means in the upper section, the duct means comprising a first manifold located on the wall of the upper section below the uppermost part of that section and having several spaced, hooded openings through the wall into the interior of the upper section;
an exhaust fan to withdraw through the duct means substantially all odors from the biowaste material and the mixture;
a second manifold above the duct means manifold and having spaced openings along the uppermost interior wall of the upper section;
a connection from the second manifold to a source of water; and
an automatically controlled valve connected to the second manifold to control the flow of water through the second manifold to clean the interior of the biowaste receiver.

5. Apparatus for handling biowaste material in substantial isolation to limit the flow of odors from the material, the apparatus comprising:
a biowaste receiver comprising an upper section shaped like a toilet bowl tapering inwardly to a constricted opening, and a bulbous chamber below the opening and of greater diameter than the opening;
means near the uppermost part of the upper section to connect a source of homogenization fluid to direct the flow of that fluid down the interior wall of the upper section and into the chamber with the biowaste material;
sensor means to respond when the total quantity of solid material and homogenization fluid in the chamber reaches a certain level;
agitation means in the bulbous chamber to be automatically energized when the sensor responds and to agitate the solid material and fluid to form a substantially homogeneous mixture;
sampling mechanism comprising a turret to support a plurality of vacutainers adjacent the chamber;
an injection needle attached to the wall of the chamber at a lower level than the sensor and extending toward the sampling mechanism;
automatic stepping mechanism controlling the turret to feed one vacutainer at a time into engagement with the needle to receive an automatic injection of the mixture and then withdraw the vacutainer from the needle;
a second manifold located adjacent the first manifold and connected to a source of cleansing water; p1 an automatically controlled wash valve connected to the second manifold to control the flow of wash water through the second manifold and along the interior wall of the upper section of the bulbous chamber;
a third manifold extending around the upper section approximately midway between the first manifold and the constricted opening;
openings through the wall of the upper section and into the third manifold to allow air to flow from the lower part of the upper section into the third manifold;
a hood extending over each of the latter openings to prevent liquid from the first and second manifolds from entering the third manifold;
a liquid drain connected to the lowermost part of the bulbous chamber;
an automatic discharge valve connected to the drain;
an exhaust fan to draw air and odors out of the upper section through the third manifold;
a pump connected to the drain to remove liquid from the chamber and force it through the drain; and
automatic sequencing means to control the operation of the controls.

* * * * *